US010238265B2

United States Patent
Gaus et al.

(10) Patent No.: US 10,238,265 B2
(45) Date of Patent: Mar. 26, 2019

(54) CLEANING DEVICE HAVING AN ENERGY STORE

(71) Applicant: MEIKO Maschinenbau GmbH & Co. KG, Offenburg (DE)

(72) Inventors: Bruno Gaus, Offenburg (DE); Wendelin Hils, Rheinmünster (DE); Thomas Peukert, Bühl (DE); Stefan Scheringer, Offenburg (DE)

(73) Assignee: MEIKO MASCHINENBAU GMBH & CO. KG, Offenburg (DE)

( * ) Notice: Subject to any disclaimer, the term of this patent is extended or adjusted under 35 U.S.C. 154(b) by 10 days.

(21) Appl. No.: 15/336,025

(22) Filed: Oct. 27, 2016

(65) Prior Publication Data

US 2017/0042402 A1 Feb. 16, 2017

Related U.S. Application Data

(63) Continuation of application No. 14/105,510, filed on Dec. 13, 2013, now abandoned, which is a (Continued)

(30) Foreign Application Priority Data

Jun. 16, 2011 (DE) .......................... 10 2011 077 660

(51) Int. Cl.
*H02J 9/00* (2006.01)
*A47L 15/00* (2006.01)
(Continued)

(52) U.S. Cl.
CPC ....... *A47L 15/0047* (2013.01); *A47L 15/0076* (2013.01); *A47L 15/241* (2013.01);
(Continued)

(58) Field of Classification Search
CPC ............................... A47L 15/4208; H02J 9/00
(Continued)

(56) References Cited

U.S. PATENT DOCUMENTS 6,153,949 A * 11/2000 Soderhall .............. H02J 7/0065
307/125
6,966,323 B2 11/2005 Deiss et al.
(Continued)

FOREIGN PATENT DOCUMENTS

DE 10147765 C1 10/2002
DE 10348344 A1 5/2005
(Continued)

OTHER PUBLICATIONS

Notice of Opposition, EP 2720598, dated Jul. 12, 2016, 27 pages and English Translation, 27 pages.
(Continued)

*Primary Examiner* — Adi Amrany
(74) *Attorney, Agent, or Firm* — Bose McKinney & Evans LLP (57) ABSTRACT

This disclosure proposes a cleaning device for cleaning items to be cleaned. The cleaning device has at least one fluid device for applying at least one cleaning fluid to the items to be cleaned. The cleaning device has at least one electrical load. The cleaning device further has at least one electrical connection for supplying electrical energy to the cleaning device. The cleaning device further has at least one energy store. The cleaning device is designed to receive electrical energy via the electrical connection and to temporarily store said electrical energy in the energy store. The cleaning device is further designed to supply electrical energy from the energy store to the at least one electrical load.

32 Claims, 3 Drawing Sheets

Related U.S. Application Data continuation of application No. PCT/EP2012/061168, filed on Jun. 13, 2012.

(51) Int. Cl.

| | | |
|---|---|---|
| *A47L 15/42* | (2006.01) | |
| *D06F 33/02* | (2006.01) | |
| *D06F 39/00* | (2006.01) | |
| *A47L 15/24* | (2006.01) | |
| *A61L 2/18* | (2006.01) | |
| *A61L 2/22* | (2006.01) | |

(52) U.S. Cl.
CPC ....... *A47L 15/4223* (2013.01); *A47L 15/4234* (2013.01); *A47L 15/4236* (2013.01); *A47L 15/4291* (2013.01); *A61L 2/18* (2013.01); *A61L 2/22* (2013.01); *D06F 33/02* (2013.01); *D06F 39/006* (2013.01); *H02J 9/00* (2013.01); A47L 15/0078 (2013.01); A47L 2401/34 (2013.01); A47L 2501/05 (2013.01); A47L 2501/06 (2013.01); A47L 2501/12 (2013.01); A47L 2501/24 (2013.01); A47L 2501/30 (2013.01); A47L 2501/32 (2013.01); Y02B 30/52 (2013.01); Y02B 40/42 (2013.01); Y02B 40/54 (2013.01)

(58) Field of Classification Search
USPC ...................................................... 307/44, 48
See application file for complete search history.

(56) References Cited

U.S. PATENT DOCUMENTS

| | | | | |
|---|---|---|---|---|
| 6,977,448 | B2* | 12/2005 | Kanouda | H02J 9/061 307/52 |
| 7,408,272 | B2* | 8/2008 | Marquet | H02J 7/0054 307/48 |
| 7,884,498 | B2 | 2/2011 | Ecker et al. | |
| 7,952,231 | B1* | 5/2011 | Zansky | H02J 7/34 307/44 |
| 8,307,839 | B2 | 11/2012 | Peukert et al. | |
| 8,548,635 | B2* | 10/2013 | Watson | G06Q 50/06 700/295 |
| 9,450,406 | B2* | 9/2016 | Palmer | H02J 3/32 |
| 2003/0025395 | A1 | 2/2003 | Peterson | |
| 2005/0162017 | A1* | 7/2005 | Chin | G06F 1/266 307/44 |
| 2006/0260335 | A1* | 11/2006 | Montuoro | F25B 49/02 62/236 |
| 2007/0104608 | A1 | 5/2007 | Gaus et al. | |
| 2008/0047502 | A1* | 2/2008 | Morse | C25B 1/12 123/3 |
| 2008/0283099 | A1* | 11/2008 | Peukert | A47L 15/4291 134/99.1 |
| 2009/0094173 | A1* | 4/2009 | Smith | G01R 21/1335 705/412 |
| 2009/0120465 | A1* | 5/2009 | Peukert | A47L 15/241 134/30 |
| 2009/0242005 | A1* | 10/2009 | Gaus | A47L 15/4285 134/57 D |
| 2009/0313767 | A1 | 12/2009 | Tanner et al. | |
| 2010/0132748 | A1 | 6/2010 | Kessler et al. | |
| 2010/0133908 | A1* | 6/2010 | Weng | G06F 1/266 307/48 |
| 2011/0023910 | A1 | 2/2011 | Dirschus | |
| 2011/0094897 | A1* | 4/2011 | Chiang | F17C 3/10 206/0.7 |
| 2011/0125337 | A1* | 5/2011 | Zavadsky | G06F 1/263 700/291 |
| 2012/0057379 | A1* | 3/2012 | Aiello | H02M 1/36 363/49 |
| 2012/0061375 | A1* | 3/2012 | Cadima | H02J 9/005 219/391 |
| 2012/0064421 | A1* | 3/2012 | Tamura | C01B 3/323 429/423 |
| 2012/0206108 | A1* | 8/2012 | Waring | H02J 3/14 320/137 |
| 2012/0208100 | A1* | 8/2012 | Suyama | C04B 35/573 429/422 |
| 2012/0271468 | A1* | 10/2012 | Doljack | H02J 9/005 700/286 |
| 2012/0296481 | A1* | 11/2012 | Iwamoto | H02J 3/14 700/286 |
| 2012/0319491 | A1* | 12/2012 | Borras | H02J 3/06 307/80 |
| 2013/0134780 | A1* | 5/2013 | Parsonnet | H02J 3/005 307/25 |
| 2013/0180553 | A1* | 7/2013 | Gaus | A47L 15/483 134/105 |
| 2013/0300194 | A1* | 11/2013 | Palmer | H02J 3/32 307/23 |

FOREIGN PATENT DOCUMENTS

| | | |
|---|---|---|
| DE | 102004046758 A1 | 4/2006 |
| DE | 102007014425 A1 | 9/2008 |
| DE | 102007053381 B3 | 4/2009 |
| DE | 102009035668 A1 | 2/2011 |
| EP | 1088927 A1 | 4/2001 |
| EP | 1253696 A1 | 10/2002 |
| EP | 2057928 A2 | 5/2009 |
| EP | 2286707 A2 | 2/2011 |
| WO | WO 2010/054820 A2 | 5/2010 |
| WO | WO 2011/053408 A2 | 5/2011 |

OTHER PUBLICATIONS

English Translation, International Preliminary Report on Patentability, PCT/EP2012/061168, dated Dec. 19, 2013, 11 pages.
International Search Report, PCT/EP2012/061168, dated Nov. 29, 2012, 3 pages.

\* cited by examiner

CLEANING DEVICE HAVING AN ENERGY STORE

RELATED APPLICATIONS

This application is a continuation of U.S. patent application Ser. No. 14/105,510, filed Dec. 13, 2013, which is a continuation of International Application PCT/EP2012/061168, filed Jun. 13, 2012, which claims priority to DE 10 2011 077 660.5, filed Jun. 16, 2011, all of which are hereby incorporated herein by reference in their entireties.

BACKGROUND

The invention relates to a cleaning device and to a method for cleaning items to be cleaned. Cleaning devices and methods of this kind are employed in various fields in order to apply at least one cleaning fluid to items to be cleaned and thereby to clean said items. Examples of an application of cleaning devices of this kind include dishwashing, both in the private sector and in the commercial sector, and also the cleaning of vessels for receiving human excreta, for example pans, bedpans or similar vessels, or else other types of care utensils, for example for hospitals or care facilities.

Numerous cleaning devices are known which are designed to clean items to be cleaned by means of at least one cleaning fluid. Examples of cleaning devices of this kind are described in DE 10 2004 046 758 A1, in DE 10 2007 053 381 B3 or else in DE 10 2009 035 A1, wherein reference is predominantly made to dishwashers in said documents. Cleaning apparatuses for cleaning pans, bedpans or similar vessels for receiving human excreta are disclosed, for example, in DE 103 48 344 A1. Cleaning apparatuses of this kind are often also called cleaning and disinfection apparatuses.

Cleaning apparatuses such as washers or cleaning and disinfection apparatuses usually have one or more electrical loads. These loads can have, for example, one or more motors or one or more heaters, for example in the form of boilers or flow heaters. Depending on the requirements of the processes being executed, these loads can be switched on individually or in any desired combination, for example in accordance with a program sequence of the cleaning apparatus. Depending on the program sequence, an amount of electrical energy which is sometimes very considerable is required for this.

Accordingly, it is becoming increasingly important to save energy, in particular in the field of commercial dishwashing, but also in the field of cleaning and disinfection apparatuses and also in the domestic field. By way of example, DE 10 2004 046 758 A1 describes a method and an arrangement for operating washers in an energy-saving manner. In this document, a group of electrical load elements of a washer are assigned a maximum total electrical power. An optimum combination of power levels is selected in a requirement determination step, depending on an operating state of the washer, wherein, for each load element of the washer, the selected power level is matched to the power requirement of the load element in the operating state, and wherein the received total power of all of the load elements does not exceed the permissible maximum total electrical power.

DE 10 2007 053 381 B3 discloses a dishwasher having a latent heat store. In this case, a heat recovery device is used, said heat recovery device drawing heat from moist air from a cleaning chamber of the cleaning apparatus and returning said heat to the cleaning apparatus by means of a first cooling fluid. The cleaning apparatus has a cooling fluid line having at least one return path and also at least one heat storage path with at least one latent heat store. The cleaning apparatus is designed to conduct the first cooling fluid to the cleaning chamber and/or into a fluid tank, after it has flowed through the heat recovery device, via the return path in at least one operating state. The cleaning apparatus is further designed to supply the first cooling fluid to the latent heat store via the heat storage path in at least one standby mode.

DE 10 2009 035 668 A1 discloses a cleaning device for cleaning items to be cleaned. The cleaning device comprises at least two loads. The cleaning device has a modular controller which comprises a machine controller and at least one contactless control element. In this case, at least one cleaning program can be carried out, wherein the contactless control element supplies energy to at least one of the loads in a variable manner. The machine controller can provide at least two different drive strategies for the cleaning device, wherein each drive strategy comprises information about energies required by the loads. The machine controller can transmit information about the energies required by the associated loads to the contactless control element via at least one bus system in accordance with a selected drive strategy. The contactless control element can supply the respectively required energy to at least one associated load.

In spite of some advantages which result from the known energy-saving concepts, a considerable amount of current and/or power can be drawn from an electrical power supply system in the building, like before. If, for example, all of the loads are switched on at the same time, the amount of power consumed can be from 3 kW to 12 kW, for example, in conventional batch dishwashers, that is to say commercial dishwashers comprising a stationary washing process. The power consumption is typically a maximum of from 15 kW to 70 kW in conveyor-type dishwashers. The maximum power consumption usually observed in cleaning and disinfection apparatuses when all of the loads are switched on at the same time is from 4 kW to 5 kW.

Electrical feed lines of the cleaning apparatuses have to be designed for maximum occurring levels of electrical power consumption, for example for said values, in the building. In addition, the operator of the cleaning device has to ensure, usually by contractual agreement with his power supplier, that the corresponding power supply and power output is ensured. The costs both of installation in the building and also of the coverage of the power supply contract with the energy supplier generally increase as the level of the maximum consumed power increases. For example, locking systems which are permanently set up and are described in DE 10 2004 046 758 A1 or in DE 10 2009 035 668 A1 are generally able to ensure that not all of the loads are switched on at the same time. Furthermore, a controller of the cleaning apparatus can be set by means of permanently set-up locking systems or else variable locking systems in such a way that the consumed power is allocated to the individual loads in a variable manner depending on requirements. Nevertheless, there is still considerable potential for improvement and optimization, in particular in respect of the high maximum consumed powers. These maximum powers generally result in high costs for the operator, both in terms of electrical installation and also in terms of the contractual arrangements with the corresponding energy suppliers. High maximum powers of this kind are also unfavorable from environmental aspects. Many of the known strategies for limiting the consumed powers naturally also limit the power of the cleaning apparatus in which these strategies are employed.

SUMMARY

The present disclosure provides a cleaning device and a method for cleaning items to be cleaned, which cleaning device and method at least largely avoid the disadvantages of known devices and methods of this kind. These teachings allow a reduction in maximum electrical power consumption by the cleaning apparatuses without having a considerable adverse effect on the power of the cleaning apparatus.

A first aspect of the present disclosure proposes a cleaning device for cleaning items to be cleaned. A second aspect of the present disclosure proposes a method for cleaning items to be cleaned. In this case, the cleaning device can be designed to carry out the method according to this disclosure, and/or the method can be carried out using a cleaning device according to this disclosure. Accordingly, reference can be made to the description of optional refinements of the method in respect of possible refinements of the cleaning device, and vice versa.

By way of example, the cleaning device, as will be explained in greater detail below, can have at least one controller, for example a central or decentral machine controller which can be designed, for example by programming, to implement the method. By way of example, this machine controller can comprise at least one data-processing device, optionally with one or more volatile and/or non-volatile data stores, wherein the data-processing device can be designed, for example by programming, to actuate the cleaning device in order to carry out a method according to this disclosure. By way of example, the data-processing device can be designed to carry out at least one cleaning program having at least two cleaning program steps. As an alternative or in addition, it is also possible for the controller to be designed to control the cleaning device in at least two different operating states, as will be explained in greater detail below.

The cleaning apparatus and the method are used for cleaning items to be cleaned. These items to be cleaned may be, in principle, any items which can be cleaned by means of a cleaning fluid, that is to say a gaseous or liquid medium. The items to be cleaned can include, in particular, dishes and/or other articles which are designed to prepare, store or serve food and drinks. For example, the dishes can be selected, in particular, from the group comprising: cups, plates, cutlery, glasses, tumblers, bowls, pots and pans and trays. As an alternative or in addition, the items to be cleaned can also originate from other sectors, in particular the medical sector and/or in the care of the sick and elderly. For example, the items to be cleaned can comprise, in particular, one or more vessels for receiving human or animal excreta, in particular chamber pots, bedpans, pans and urine bottles, in particular vessels with a capacity of at least 100 ml, preferably at least 500 ml. Once again as an alternative or in addition, the items to be cleaned can comprise, for example, other medical apparatuses and/or machine parts.

Within the scope of the present disclosure, cleaning is generally understood to mean a method in which an article is completely or partially freed from impurities, wherein these impurities can be of an organic and/or inorganic nature, and wherein these impurities can also comprise, in particular, one or more types of microorganism. In particular, these impurities can be impurities which adhere to the article and/or impurities which are contained in at least one cavity in the article. The impurities can comprise, in particular, food residues and/or human or animal excreta. As an alternative or in addition, cleaning can also comprise complete or partial decontamination, that is to say completely or partially freeing the article of microorganisms, in particular disinfection and/or sterilization.

The method is carried out in such a way that at least one cleaning fluid is applied to the items to be cleaned by means of at least one fluid device, and the cleaning device comprises at least one fluid device for applying at least one cleaning fluid to the items to be cleaned. A cleaning fluid can be understood to mean a liquid and/or gaseous medium which is designed to remove adhering impurities from the items to be cleaned and/or to disinfect or even to sterilize the items to be cleaned. In particular, the cleaning fluid can comprise at least one aqueous cleaning fluid, in particular a rinse liquid which comprises water and also one or more additives of at least one detergent and/or at least one rinse aid and/or at least one disinfectant. As an alternative or in addition, the cleaning fluid can furthermore also comprise, for example, one or more non-aqueous media and/or one or more gaseous media. As an alternative or in addition, the cleaning fluid can comprise at least one vapor, in particular for disinfecting and/or sterilizing the items to be cleaned. The cleaning fluid can, in particular, comprise superheated vapor, that is to say steam, optionally with the addition of one or more assistant, for example at least one disinfectant.

A fluid device is understood to mean, in principle, any desired device which is designed to apply the cleaning fluid to the items to be cleaned. In particular, the fluid device can have at least one opening to which the cleaning fluid can be supplied, for example via at least one supply line, and from which the cleaning fluid can be discharged. In particular, the fluid device can have at least one nozzle and/or at least one nozzle system from which the cleaning fluid can be discharged, for example in the form of a jet, in order to strike the items to be cleaned. The fluid device can have, for example, one or more nozzle arms and/or one or more nozzle systems.

The cleaning device also has at least one electrical load, and the method is carried out in such a way that at least one electrical load is used in the method. An electrical load is understood to mean, in general, a device which is designed to receive electrical energy and, for example, convert this electrical energy into other forms of energy and/or into computational power and/or into stored information. In particular, the at least one load can be designed to convert electrical energy into mechanical energy, for example kinetic energy and/or pressure. As an alternative or in addition, the at least one load can be designed to convert all or some of the electrical energy into thermal energy, for example in order to heat the at least one cleaning fluid and/or to heat the items to be cleaned.

The at least one load can be selected, for example, from the group comprising: a heating device, in particular a boiler, a heating coil or a flow heater; a motor, in particular a motor for driving a transportation system for the items to be cleaned and/or a motor for driving a movement of the fluid device; a controller for controlling the cleaning device, in particular a data-processing device and/or a data storage means; a pump, in particular a pump for conveying the cleaning fluid and/or a pump for applying the cleaning fluid to the items to be cleaned; a fan, in particular a fan for drawing hot air from a cleaning chamber of the cleaning device by suction and/or a fan for applying at least one gaseous medium to the items to be cleaned, in particular a hot-air fan. Other refinements of the loads and combinations of said options and/or other options are also possible.

The cleaning device also has at least one electrical connection for supplying electrical energy to the cleaning device, and the method is configured in such a way that at least one electrical connection is used for supplying electrical energy to the method. An electrical connection is understood to mean, in principle, any desired device which can supply electrical energy to the cleaning device or for use in the method. In this case, an electrical connection can be, in particular, a permanent connection in the building, for example a permanently-wired building connection with at least one power supply cable. However, the electrical connection can also be designed, in principle, in a detachable manner, for example in the form of at least one male and/or female plug which can be connected, for example, to at least one plug in the building and/or at least one cable. As an alternative or in addition to a cable-bound connection, a wireless power supply is also feasible in principle. By way of example, the connection can be designed to receive an electrical power of at least 200 W, in particular at least 1 kW, and particularly preferably at least 5 kW, from at least one power supply and to supply said power to the cleaning device or the method.

The cleaning device has at least one energy store, and the method is carried out in such a way that at least one energy store is used. Within the scope of the present disclosure, an energy store is understood to mean, in principle, any desired device which is designed to receive energy, to store this energy and to output this energy again. Examples of energy stores of this kind will be explained in greater detail below. The energy store can act, in particular, as an electrical buffer and/or be designed as an electrical buffer, that is to say as a device which is suitable for or designed for temporarily storing electrical energy.

The cleaning device and the method are further designed in such a way that electrical energy is received via the electrical connection and temporarily stored in the energy store. In this case, temporary storage is understood to mean, in general, storage of energy which serves the purpose of subsequent use of the energy. In this case, the electrical energy received via the electrical connection can, as will be explained in greater detail below, be temporarily stored in the energy store in the form of electrical energy and/or in at least one other form of energy, for example in the form of heat and/or in the form of chemical energy and/or in the form of mechanical energy.

The cleaning device and the method are further designed in such a way that the at least one electrical load is at least partly supplied with electrical energy from the temporary store, in particular in at least one operating phase and/or in at least one program step. In particular, the cleaning device and the method can be designed in such a way that electrical energy can be received via the electrical connection and temporarily stored in the energy store, before the energy is supplied to one or more electrical loads for the first time.

Electrical energy from the at least one energy store can be directly supplied to the at least one electrical load, with the result that the energy which is stored in the energy store is supplied to the electrical load directly and/or indirectly, for example after conversion of the energy which is received in the energy store into at least one other form of energy. For example, as explained above, the energy in the temporary store can also be temporarily stored in non-electrical form. In this case, as will be explained in greater detail below by way of example, this temporarily stored energy should first be converted into electrical energy, before this electrical energy is then supplied to the at least one electrical load. The electrical energy which is received from the electrical connection can be directly and/or indirectly temporarily stored and electrical energy from the temporary store can be directly and/or indirectly supplied to the electrical load, that is to say as a result of energy being temporarily stored in the form of electrical energy and/or in the form of non-electrical energy, in the latter case with corresponding conversion between the forms of energy.

As explained above, the cleaning device can be selected, in particular, from the group comprising: a dishwasher, in particular a batch dishwasher and/or a conveyor-type dishwasher, in particular a dishwasher for commercial use; a cleaning and disinfection apparatus, for example for cleaning vessels for receiving human excreta and/or for cleaning other types of medical equipment. The dishwasher can be designed, for example, as a single-chamber dishwasher or else as a multi-chamber dishwasher. Within the scope of the present disclosure, a batch dishwasher can be understood to mean, in particular, a dishwasher with a stationary washing process, that is to say a dishwasher in which the items to be cleaned remain in a cleaning chamber during cleaning, wherein several treatment steps can be carried out one after the other within the scope of a cleaning program. A commercial dishwasher is understood to mean, in general, a dishwasher which has at least two tanks for separately receiving and/or treating cleaning fluid and which is designed to clean relatively large quantities of dishes with a high throughput. In respect of possible refinements of the single-chamber dishwasher and/or the conveyor-type dishwasher, reference can be made, for example, to the prior art cited above which can be modified in accordance with this disclosure. The cleaning and disinfection apparatus can be designed, in general, to clean vessels which are designed to receive relatively large quantities of waste, for example quantities of liquid and/or solid excreta in quantities of at least 100 ml, in particular at least 200 ml or even at least 500 ml or at least 1 l or at least 2 l. Accordingly, the cleaning and disinfection apparatus can have, for example, at least one outflow which is designed to discharge said quantities of liquid, for example an outflow with a siphon bend. Reference can be made, for example, to DE 103 48 344 A1, which is cited above, for possible refinements of the cleaning and disinfection apparatus, wherein the cleaning and disinfection apparatus described in said document can be modified in accordance with this disclosure.

In general, the cleaning device can have, for example, at least one cleaning chamber in which cleaning liquid can be applied to the items to be cleaned. The chamber can be of open design and, for example, only prevent relatively large quantities of liquid or relatively large quantities of vapor escaping to the surrounding area, or can be of closed design, with the result that liquid and/or vapor is completely prevented from escaping from the chamber to a working environment. One or else several chambers can be provided. The at least one chamber can be closable, for example, by at least one closure, for example at least one loading flap. However, as an alternative or in addition, the at least one chamber can also have, for example, at least one tunnel, as in the case of the above-described conveyor-type dishwasher according to the prior art for example.

Further optional refinements relate to a controller for the energy consumption and/or a controller for the supply of electrical energy to the at least one electrical load. The measures described in the text which follows can be implemented, for example in respect of equipment, by, as explained above, the cleaning device having at least one controller, for example a controller having at least one data-processing device which is designed to carry out the described refinements. Accordingly, the proposed method can have method steps for implementing the optional features.

For example, the cleaning device can be designed, in particular, to selectively, for example as prescribed by the controller, supply electrical energy from the energy store and selectively directly supply electrical energy which is received via the electrical connection to the at least one electrical load. By way of example, the cleaning device can have at least one switching element which can switch continuously or in several stages between supplying electrical energy from the energy store to the electrical load and supplying electrical energy from the electrical connection to the electrical load without temporarily storing said electrical energy in the energy store. Continuous switchover can be understood to mean, for example, switching between a state in which only electrical energy from the energy store is supplied to the electrical load and a state in which only electrical energy from the electrical connection is supplied to the electrical load without temporarily storing said electrical energy in the energy store. Switchover in one or more stages can be understood to mean, for example, a switching operation in which at least one further state exists in addition to the two said states, both electrical energy from the electrical connection, without temporary storage of said electrical energy in the energy store, and also electrical energy from the energy store being supplied to the electrical load in said further state. Continuous switching can be realized by, for example, a mixing ratio of the supply of electrical energy from the electrical connection, without temporary storage of said electrical energy in the energy store, and of electrical energy from the energy store to the electrical load being variably settable, in particular continuously, for example in a predefined mixing ratio range. If a plurality of electrical loads are provided, said optional at least one switching element, which can set the type and/or the mixing ratio of the supply of energy to the electrical load, can be provided for an individual one of said electrical loads, for several selected electrical loads or else for all of the electrical loads together in order to set the supply of energy. It is also possible to provide a plurality of switching elements of said type which can each set the supply of energy for one or more electrical loads in said manner.

By way of example, the electrical connection can be directly or indirectly electrically connected to the energy store, and the energy store can be directly or indirectly connected to the at least one electrical load. In addition, for example, the electrical connection can optionally be directly or indirectly connected to the electrical load, for example via at least one electrical bypass line which bypasses the energy store. The cleaning device can have, for example, as described above, at least one switching element, for example a switch and/or another type of apparatus which controls and/or regulates a flow of energy via the energy store and/or so as to bypass the energy store in the direction of the at least one electrical load. By way of example, this device can have at least one switching element which can be designed to influence the flows of energy over said paths.

As already explained above, the cleaning device can also be designed to supply electrical energy from the energy store and electrical energy which is received directly via the electrical connection to the electrical load at the same time. This can also be performed, for example, using the at least one optional switching element. For example, a refinement can be realized, in which both energy which was previously temporarily stored in the energy store and also electrical energy which is received directly from the electrical connection is supplied to one or more loads at the same time. If several loads are provided, the cleaning device can, for example, also be configured in such a way that energy which is received directly via the electrical connection is supplied to one or more loads, without temporary storage of said energy in the energy store, whereas, as an alternative or in addition, electrical energy from the energy store is supplied to one or more further loads. The cleaning device can be designed, in particular, to change a ratio between the electrical energy from the energy store and the electrical energy which is received directly via the electrical connection without temporary storage of said electrical energy in the energy store, in which ratio said electrical energy is applied to the electrical load. By way of example, this ratio can be configured in a variable manner given mixing of application of electrical energy from the energy store and electrical energy from the electrical connection continuously or in one or more different stages. In particular, the cleaning device can be designed to match the ratio to a current operating state.

The cleaning device can also be designed, in particular, to be operated in at least two different operating states. By way of example, the cleaning device can have, as explained above, at least one controller which is designed to set at least two operating states for the cleaning device.

In this case, an operating state is understood to mean, in general, a state of the cleaning device which is characterized by a set of operating parameters of the cleaning device. By way of example, these operating parameters can describe the currently assumed state for several or all of the elements of the cleaning device which can assume different states. Said states may be, for example, electrical and/or mechanical and/or thermal states of one or more elements of the cleaning device and/or of the cleaning fluid and/or of the items to be cleaned. These operating parameters can comprise, for example, rotation speeds of motors and/or pumps, current levels of electrical power consumption, speed in a transportation device, power outputs by the heating devices, current temperatures of one or more cleaning fluids, ambient temperatures in a cleaning chamber of the cleaning device or similar operating parameters. The cleaning device can be designed, for example by means of the at least one controller, to actively influence several or all of these operating parameters and/or to detect these parameters.

In particular, the cleaning device can be designed in such a way that the at least one load has a different electrical power consumption in the at least two different operating states. For example, a first operating state can exist, in which the load has a first electrical power consumption, and a second operating state can exist, in which the load has a second electrical power consumption which is different from the first.

In this case, at least two different operating states can also be provided, in which the energy store is used differently. For example, at least a first operating state, in which the energy store is charged, and at least a second operating state, in which the energy store is discharged, can be provided. For example, the cleaning device can be designed, in particular, such that electrical energy is received via the electrical connection and the energy store is charged with electrical energy in at least a first operating state. Furthermore, electrical energy can be drawn from the energy store and supplied to the electrical load in at least a second operating state. Mixed forms are also possible, for example mixed forms in which the energy store and/or at least one energy store is/are charged and electrical energy is drawn from the energy store and/or from at least one energy store at the same time.

The first operating state, in which the energy store is charged, can, in particular, also comprise a downtime of the cleaning device, wherein no cleaning liquid is applied to the items to be cleaned during the downtime. This downtime can comprise, for example, a standby mode which can be carried out, for example, during intervals in washing and/or overnight or at the weekend. This downtime can be configured in such a way that only application of the cleaning liquid to the items to be cleaned is stopped, but one or more further loads of the cleaning device can continue to remain active, for example a transportation device and/or a fan. As an alternative, the downtime can also be configured in such a way that all of the loads of the cleaning device are at a stop and/or in a standby state in which no power is consumed by these loads and/or only a minimum amount of power is consumed by these loads. During this downtime, the energy store can, for example, be charged with electrical energy which is received from the electrical connection.

The second-mentioned operating state, in which electrical energy is drawn from the energy store and the energy is supplied to the at least one load, can be performed in such a way that the load is supplied with power only from the energy store or, as an alternative, that electrical energy which is received via the electrical connection is additionally supplied to the load. For example, the cleaning device can be designed to additionally receive electrical energy via the electrical connection and to supply said electrical energy to the electrical load, in addition to a supply from the energy store, in the second operating state. In this way, as will be explained in greater detail below, a maximum power consumption via the electrical connection can be reduced for example, with the result that, for example, the maximum electrical power consumption by the cleaning device can be reduced, for example by at least 10%, preferably by at least 20% or more, in comparison to a cleaning device with identical loads but without an energy store.

In particular, the cleaning device can be designed to limit an electrical power which is received via the electrical connection to a maximum power. This power limiting can be performed, for example, by at least one corresponding monitoring device which detects a current power consumption, and/or by means of at least one limiting device which limits a current power consumption to a maximum power consumption. In this respect, reference can be made, for example, to the abovementioned prior art, in particular to DE 10 2009 035 668 A1. The cleaning device can be designed, in particular, in such a way that, in the same mode, and with the option of energy from the energy store and also energy which is directly received via the electrical connection being supplied to the electrical load, the power consumption is limited to a prespecified maximum power which is lower than a maximum electrical power of an identical cleaning device without an energy store.

The cleaning device can further be designed to at least temporarily store in the energy store a difference between the prespecified maximum power and a power which is currently required in total by the load, in particular if a power which is currently required in total by the load is lower than the maximum power. The energy difference can be stored in this way, for example, permanently or only during one or more charging phases during which the energy store can be charged.

Further possible refinements of this disclosure relate to refinements of the energy store. For example, the energy store can have a capacity for temporarily storing energy of at least 10 Wh, and preferably of at least 100 Wh or at least 1 kWh, particularly preferably of at least 10 kWh or even at least 30 kWh.

As stated above and as will be explained in greater detail below, this energy can be stored, for example, in electrical form and also in non-electrical form. In particular, the energy store can be designed to temporarily store said quantities of energy for a period of several minutes, preferably of at least 10 minutes, preferably of at least 1 hour, and particularly preferably of at least 10 hours.

As stated above, the energy store, wherein one or more energy stores can be provided, can be designed as a whole or in part to temporarily store electrical energy and/or one or more other forms of energy. If a plurality of energy stores are provided, it is also possible, for example, for one or more energy stores to be designed to temporarily store electrical energy and for one or more energy stores to temporarily store one or more other forms of energy.

In particular, the energy store can therefore have at least one electrical energy store. This electrical energy store can be selected, in particular, from the group comprising: a rechargeable battery, in particular a lead-acid rechargeable battery, an NiCd rechargeable battery, an NiMH rechargeable battery or a lithium-ion rechargeable battery; and a capacitor, in particular a so-called supercapacitor or "supercap." Within the scope of the present disclosure, a supercap or a supercapacitor is generally understood to mean a double-layer capacitor with a high capacitance which is based on a disassociation of ions in a liquid electrolyte, which ions form a dielectric of few atomic layers and a large electrode surface. By way of example, supercaps can have an energy density of at least 0.5 Wh/kg, of at least 1 Wh/kg, and in particular of at least 4 Wh/kg. Supercaps of this kind are commercially available in various forms. Combinations of said electrical energy stores and/or other types of energy stores can also be used in principle. The electrical energy store can comprise at least one energy converter which is designed to initially convert electrical energy which is received via the electrical connection, before said electrical energy is temporarily stored in the form of electrical energy. By way of example, this at least one energy converter can comprise at least one rectifier and/or at least one transformer. Furthermore, as an alternative or in addition, the electrical energy store can have at least one electrical energy converter, which converts the electrical energy which is stored in the electrical energy store, before it is supplied to the at least one electrical load, for example an inverter and/or a transformer.

As stated above, the energy store can further comprise at least one non-electrical energy store as an alternative or in addition to at least one electrical energy store. The energy store can optionally also comprise at least one energy converter in this case, wherein the energy converter can be designed to perform conversion between electrical energy and at least one non-electrical form of energy, wherein the non-electrical form of energy can be stored in the non-electrical energy store. By way of example, the non-electrical energy store can comprise at least one first energy converter which is designed to convert the electrical energy which is received via the electrical connection into at least one non-electrical form of energy which can be stored in the non-electrical energy store. As an alternative or in addition, the energy store can comprise at least one second energy converter which is designed to convert the non-electrical form of energy, which is stored in the non-electrical energy store, into electrical energy before it is supplied to the at least one load.

The configuration of the at least one optional energy converter can be dependent, in particular, on the non-electrical form of energy. The energy converter can have, for example, a mechanical-electrical energy converter and/or a thermal-electrical energy converter and/or a chemical-electrical energy converter. A thermal-electrical energy converter can comprise, for example, a heating element and/or a Peltier element and/or a Seebeck element. A mechanical-electrical energy converter can comprise, for example, an electric motor and/or a dynamo and/or a generator. A chemical-electrical energy converter can comprise, for example, at least one electrolysis cell and/or at least one fuel cell.

In one possible refinement, the non-electrical energy store can comprise, for example, at least one heat store. This heat store can have, for example, at least one element with a specific heat capacity $c_p$ or $c_v$ of at least 1000 J/(kg·K), preferably of at least 2000 J/(kg·K), in particular of at least 4000 J/(kg·K) and particularly preferably of at least 5000 J/(kg·K). By way of example, the heat store can have at least one block and/or at least one reservoir of at least one material with said heat capacity, for example a copper block and/or a water tank.

The heat store can be selected from the group comprising a direct heat store and a latent heat store. In this case, a direct heat store is to be understood to mean a heat store which can receive and store heat without a change in phase taking place in the process. For example, at least one direct heat store in the form of at least one water tank, filled with water, preferably with a thermal insulation and/or with at least one heat pump can be provided. As an alternative or in addition, the direct heat store can also have at least one block of a material for receiving heat, preferably a material with said heat capacity. A block of at least 5 kg, preferably of at least 10 kg, and particularly preferably of at least 40 kg of said material can be present, for example. A direct heat store is to be understood, in general, to mean an element which can directly receive said heat and store said heat in the form of heat.

As an alternative or in addition to a direct heat store, the heat store can also have at least one latent heat store. Within the scope of the present disclosure, a latent heat store is to be understood to mean, in general, a device which has at least one material which can undergo at least one change in phase in a reversible manner. For example, the latent heat store can receive heat, carry out a change in phase, and in this way temporarily store the thermal energy, generally as another form of energy, in order to then again be able to carry out the same change in phase or another change in phase, in the reverse direction, and in the process be able to completely or partially emit the received heat again. Examples of changes in phase are melting processes, dissolving processes, absorption processes or crystallization processes. Phase-change materials of this kind, which can also be used within the scope of the present disclosure, are, for example, salt stores, such as sodium acetate trihydrate in particular. The salt hydrate can be liquefied, for example, in water at a melting point of 58° C. and can also be present as a supercooled melt in a metastable state at lower temperatures. The salt can dissolve in its water of crystallization. Crystallization can be triggered by a crystallization nucleus, wherein heat can be released. Conversely, liquefaction can be initiated by heating the salt store. However, other types of latent heat store can also be used within the scope of the present disclosure in principle.

As an alternative or in addition to a heat store, the non-electrical energy store can comprise at least one mechanical energy store. The mechanical energy store can be selected, for example, from the group comprising a pressure store, in particular a gas pressure store and/or a spring store; and a flywheel store. Other mechanical energy stores can also be used.

As an alternative or in addition to the abovementioned options, the non-electrical energy store can further comprise at least one chemical energy store. A chemical energy store is understood to mean, in general, an energy store which is designed to receive energy and to use this received energy to start at least one chemical reaction, preferably at least one reversible chemical reaction. The chemical energy store can further be designed to carry out a reverse chemical reaction, for example a chemical back-reaction, and in the process again release energy, for example thermal energy. One example of a chemical energy store which can be used within the scope of the present disclosure is a gas store. Said gas store may be, in particular, a hydrogen store and/or at least one oxygen store. The energy store can comprise, in particular, at least one electrolysis cell and/or at least one fuel cell as the energy converter, wherein said elements can also be provided individually, or both of said elements can be provided, as energy converters. The energy store can be designed, for example, in such a way that it supplies electrical energy, which is received via the electrical connection, to an electrolysis cell, wherein at least one electrolysis reaction, for example electrolysis of water, takes place in the electrolysis cell, wherein the electrolysis products which are produced as a result, for example hydrogen and/or oxygen, can be stored. Furthermore, the energy store can comprise at least one second energy converter in the form of at least one fuel cell, wherein the electrolysis products, for example hydrogen and/or oxygen, can react by means of the fuel cell, wherein heat and/or electrical energy are/is generated, it being possible for this energy to be supplied to the electrical load directly or after further conversion into electrical energy. The electrolysis cell and the fuel cell can be designed separately, but can also be configured entirely or partially from identical components.

The proposed cleaning device and the proposed method have numerous advantages over known devices and methods of said kind. For example, energy can be stored in the energy store particularly when the cleaning device is not utilized to full capacity or, for example, during interruptions in operation and/or downtimes, in particular at night. The stored energy can then be called up from the energy store during operation of the cleaning device, for example in the event of full-load operation. As a result, the power which is supplied to the electrical loads of the cleaning device can be increased without the total electrical power which is received via the electrical connection, for example from the electrical supply system in the building, increasing, for example beyond a prespecified maximum power. Operation of this kind can also be called boost operation. A total power of the cleaning device can also be increased by this increased power which is supplied to the electrical loads, in order, for example, to achieve relatively high speeds and, as a result, relatively high throughputs in conveyor-type dishwashers.

The energy store can also be advantageously used to make the cleaning device, for example a dishwasher, ready for operation. For example, the energy store can be charged during an interval in operation, in particular at night. After the interval in operation has ended, for example in the morning, after the cleaning device is filled with cleaning fluid, a considerably higher heating power can be generated in the cleaning device given a comparatively low power consumption via the electrical connection, for example in order to heat up one or more cleaning fluids more quickly, in order to thereby make said cleaning device ready for operation more quickly, for example.

The use of the energy store and its advantages become more interesting as operation of the cleaning device becomes more non-uniform. The cleaning device can be designed, for example, to carry out at least 2, preferably at least 3, at least 4 or more cleaning programs. The cleaning programs can each comprise, for example, one or more program steps which can be carried out in succession, at the same time or even so as to overlap in respect of time. The cleaning program steps can comprise, for example, different ways in which cleaning fluid is applied to the item to be cleaned, for example application of different types of cleaning fluids, for example application of a detergent solution and application of a rinse aid solution, and optionally application of a disinfectant solution and optionally application of superheated vapor. Furthermore, the program steps can comprise application of cleaning fluids of different temperatures. Furthermore, the cleaning program steps can have one or more drying phases and/or one or more draining phases and/or one or more emptying phases (for example for emptying excretion vessels for receiving human or animal excreta).

The more complex the cleaning operation and the greater the variety of program steps in the cleaning programs, the more varied and the more non-uniform the power consumption by the electrical loads involved is in general, with the result that the use of the energy store becomes even more advantageous. For example, in the case of a dishwasher in the form of a batch dishwasher, a downtime of 90 secs or more can reduce the rating of an electrical connection in the building to 50% of the nominal value after each rack containing items to be cleaned has been washed, for example given a program time of 90 secs. Cleaning and disinfection apparatuses also generally have a highly non-uniform operating profile. For example, a washing program in cleaning and disinfection apparatuses of this kind generally lasts 5 minutes, this generally being followed by a downtime phase of 10 minutes. By virtue of the use of said energy store, the electrical connection can be changed over, for example, from a three-phase alternating current to a single-phase alternating current in the case of a cleaning and disinfection apparatus, this generally meaning a considerable simplification and at the same time possibly extending the possible range of use of the cleaning device. In this case, a cleaning and disinfection device, for example, can also be easily used in a private household which generally does not have three-phase alternating current connections.

Furthermore, the use of the energy store allows the range of fluctuation in power consumption by the cleaning device, for example a dishwasher and/or a cleaning and disinfection apparatus, to be reduced given a constant average value. For example, power for load peaks can be supplied not from the supply system, but rather from the energy store. In this way, the received electrical peak load can be reduced in relation to current values.

As stated above, there are numerous different options for realizing the energy store, it being possible to match these to the respective circumstances and requirements. For example, the energy can be stored electrically, in the form of heat, in particular in a direct and/or latent manner, mechanically or chemically. Combinations of said options can also be realized. The electrical energy stores used can be, for example, rechargeable batteries of different constructions and/or technologies, for example the abovementioned rechargeable batteries. As an alternative or in addition, one or more electrical capacitors, for example supercaps, can be used as electrical energy stores. Heat stores can be easily realized in the form of water tanks, in particular with insulation and possibly at least one heat pump. Latent heat stores in the form of salt stores can be realized in a technically simple manner, this being demonstrated by their widespread use in the form of heat packs. Mechanical stores, for example pressure stores in the form of gas pressure and/or spring stores, or flywheel stores, can also be realized in a simple manner. Chemical stores can also be realized in a reliable and secure manner and without a relatively high volume requirement, likewise with conventional technologies, by the use of electrolysis cells and fuel cells.

In the concepts known from the abovementioned prior art for increasing the energy efficiency of cleaning devices, energy which is generally already present in the cleaning device is used further or used again. For example, cleaning devices can be operated with storage systems or heat recovery apparatuses. Apparatuses of this kind can also be additionally used within the scope of the present disclosure in principle. However, in particular, electrical energy can be temporarily stored by means of the described energy store, before said electrical energy is used in the cleaning device for the first time.

This temporary storage can be used, for example, as stated above, to make said cleaning device ready for operation more quickly or to reduce a maximum power.

Overall, the following embodiments are considered to be particularly preferred within the scope of the present disclosure:

Embodiment 1: a cleaning device for cleaning items to be cleaned, wherein the cleaning device has at least one fluid device for applying at least one cleaning fluid to the items to be cleaned, wherein the cleaning device has at least one electrical load, wherein the cleaning device has at least one electrical connection for supplying electrical energy to the cleaning device, wherein the cleaning device has at least one energy store, wherein the cleaning device is designed to receive electrical energy via the electrical connection and to temporarily store said electrical energy in the energy store, and wherein the cleaning device is further designed to supply electrical energy from the energy store to the at least one electrical load.

Embodiment 2: the cleaning device according to the preceding embodiment, wherein the cleaning device is selected from the group comprising: a dishwasher, in particular a single-chamber dishwasher and/or a conveyor-type dishwasher; and a cleaning and disinfection apparatus for cleaning excretion vessels for receiving human excreta.

Embodiment 3: the cleaning device according to either of the preceding embodiments, wherein the cleaning device is designed to selectively supply electrical energy from the energy store and selectively directly supply electrical energy which is received via the electrical connection to the at least one electrical load.

Embodiment 4: the cleaning device according to one of the preceding embodiments, wherein the cleaning device is designed to simultaneously supply electrical energy from the energy store and supply electrical energy which is received directly via the electrical connection to the at least one electrical load.

Embodiment 5: the cleaning device according to the preceding embodiment, wherein the cleaning device is designed to change a ratio between the electrical energy from the energy store and the electrical energy which is received directly via the electrical connection, in which ratio said energy is supplied to the electrical load.

Embodiment 6: the cleaning device according to the preceding embodiment, wherein the cleaning device is designed to match the ratio to a current operating state.

Embodiment 7: the cleaning device according to one of the preceding embodiments, wherein the cleaning device is designed to be operated in at least two different operating states, wherein the load has a different electrical power consumption in the operating states, wherein electrical energy is received via the electrical connection and the energy store is charged with electrical energy in at least a first operating state, and wherein electrical energy is drawn from the energy store and supplied to the electrical load in at least a second operating state.

Embodiment 8: the cleaning device according to the preceding embodiment, wherein the first operating state comprises a downtime of the cleaning device, wherein no cleaning fluid is applied to the items to be cleaned during the downtime.

Embodiment 9: the cleaning device according to either of the two preceding embodiments, wherein the cleaning device is designed to additionally receive electrical energy via the electrical connection and to additionally supply said electrical energy to the electrical load in the second operating state.

Embodiment 10: the cleaning device according to one of the preceding embodiments, wherein the cleaning device is designed to limit an electrical power, which is received via the electrical connection, to a prespecified maximum power.

Embodiment 11: the cleaning device according to the preceding embodiment, wherein the cleaning device is designed to temporarily store in the energy store a difference between the prespecified maximum power and a power which is currently required in total by the load.

Embodiment 12: the cleaning device according to one of the preceding embodiments, wherein the energy store can have a capacity for temporarily storing an energy of at least 10 Wh, and preferably of at least 100 Wh or at least 1 kWh, or particularly preferably of at least 10 kWh or even at least 30 kWh.

Embodiment 13: the cleaning device according to one of the preceding embodiments, wherein the energy store has at least one electrical energy store.

Embodiment 14: the cleaning device according to the preceding embodiment, wherein the electrical energy store is selected from the group comprising: a rechargeable battery, in particular a lead-acid rechargeable battery, an NiCd rechargeable battery, an NiMH rechargeable battery or a lithium-ion rechargeable battery; and a capacitor, in particular a supercap.

Embodiment 15: the cleaning device according to one of the preceding embodiments, wherein the energy store further comprises at least one non-electrical energy store.

Embodiment 16: the cleaning device according to the preceding embodiment, wherein the energy store comprises at least one energy converter, wherein the energy converter is designed to convert between electrical energy and at least one non-electrical form of energy, wherein the non-electrical form of energy can be stored in the non-electrical energy store.

Embodiment 17: the cleaning device according to either of the two preceding embodiments, wherein the non-electrical energy store comprises at least one heat store.

Embodiment 18: the cleaning device according to the preceding embodiment, wherein the heat store is selected from the group comprising: a direct heat store, in particular a water tank, preferably having at least one thermal insulation and/or at least one heat pump; and a latent heat store, in particular a salt store.

Embodiment 19: the cleaning device according to one of the four preceding embodiments, wherein the non-electrical energy store comprises at least one mechanical energy store.

Embodiment 20: the cleaning device according to the preceding embodiment, wherein the mechanical energy store is selected from the group comprising: a pressure store, in particular a gas pressure store and/or a spring store; and a flywheel store.

Embodiment 21: the cleaning device according to one of the six preceding embodiments, wherein the non-electrical energy store comprises at least one chemical energy store.

Embodiment 22: the cleaning device according to the preceding embodiment, wherein the chemical energy store comprises at least one gas store, in particular at least one hydrogen store and/or at least one oxygen store.

Embodiment 23: the cleaning device according to either of the two preceding embodiments, wherein the energy store comprises at least one electrolysis cell and/or at least one fuel cell as the energy converter.

Embodiment 24: the cleaning device according to one of the preceding embodiments, wherein the electrical load is selected from the group comprising: a heating device for heating the at least one cleaning fluid; a pump for conveying the at least one cleaning fluid; a vapor generator for generating superheated vapor; a fan for conveying at least one vapor and/or at least one gas; and a transportation device for conveying the items to be cleaned.

Embodiment 25: a method for cleaning items to be cleaned, in particular using a cleaning device according to one of the preceding embodiments, wherein at least one cleaning fluid is applied to the items to be cleaned by means of at least one fluid device, wherein at least one electrical load is used in the method, wherein at least one electrical connection is used for supplying electrical energy to the method, wherein at least one energy store is used, wherein electrical energy is received via the electrical connection and said electrical energy is temporarily stored in the energy store, wherein electrical energy from the energy store is supplied to the at least one electrical load.

BRIEF DESCRIPTION OF THE DRAWINGS

The above-mentioned aspects of this disclosure and the manner of obtaining them will become more apparent and the invention itself will be better understood by reference to the following description of the embodiments, taken in conjunction with the accompanying drawings, wherein.

DETAILED DESCRIPTION

Figure 1:
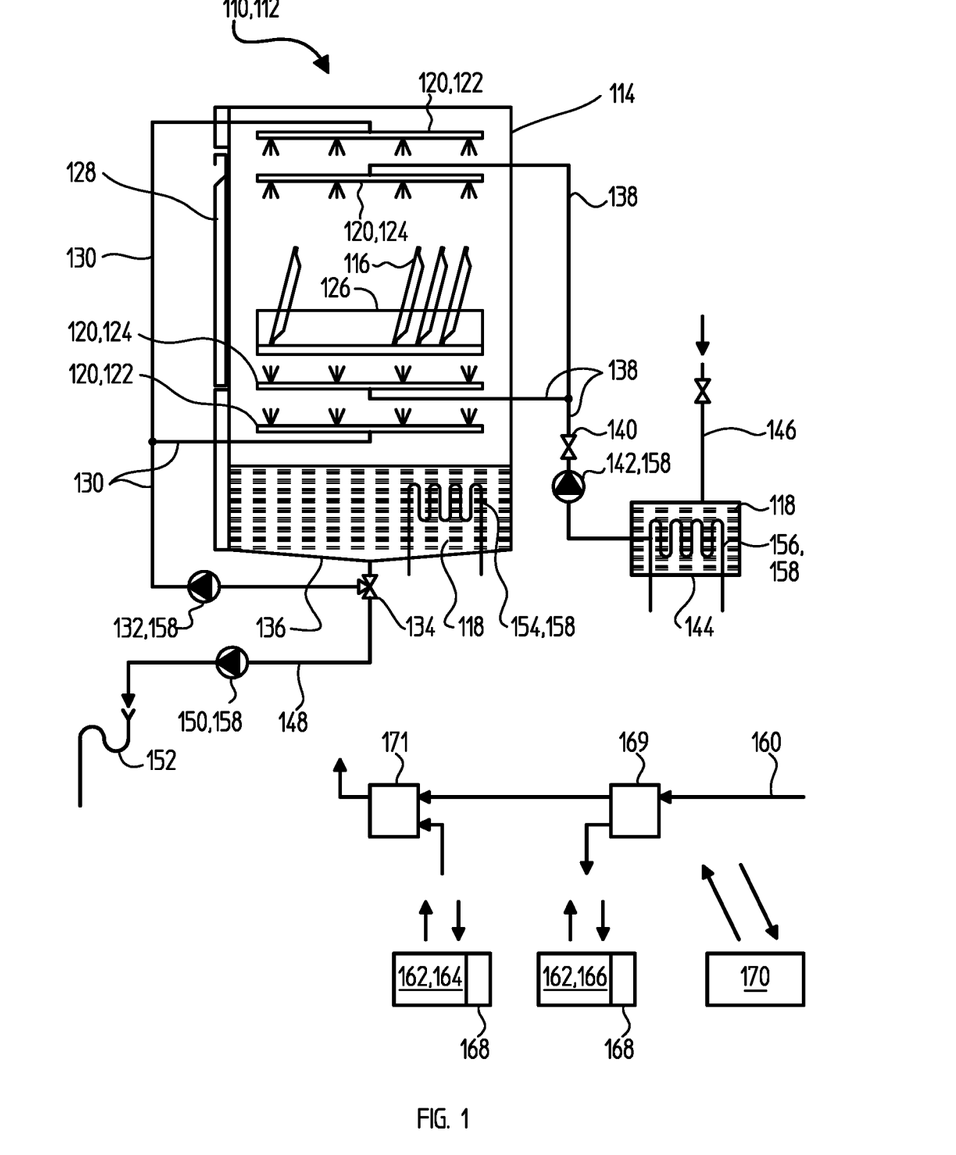
FIG. 1 shows a first exemplary embodiment of a cleaning device according to this disclosure in the form of a single-chamber dishwasher.

FIG. 1 shows a schematic sectional illustration through a first exemplary embodiment of a cleaning device 110 according to this disclosure. In this case, the cleaning device 110 is configured, by way of example, as a single-chamber dishwasher 112. Reference can be made, by way of example, to DE 10 2004 046 758 A1 for examples of possible refinements of single-chamber dishwashers 112 of this kind. However, other refinements are also possible in principle.

In the illustrated exemplary embodiment, the cleaning device 110 can comprise a cleaning chamber 114 in which cleaning fluid 118 can be applied to items 116 to be cleaned, for example dishes. One or more fluid devices 120 can be provided to perform this application, it being possible for said fluid devices to comprise, by way of example, a wash nozzle system 122 and a rinse nozzle system 124 in the illustrated exemplary embodiment. The nozzle systems 122, 124 can be arranged, for example, within the cleaning chamber 114 above and below a rack 126 in which the items 116 to be cleaned are accommodated. The cleaning chamber 114 can be loaded with the items 116 to be cleaned, for example, via a door 128, for example a front flap. The wash nozzle system 122 can be fed with cleaning fluid 118, for example a detergent solution, from a wash tank 136, which can be located, for example, in the bottom region of the cleaning chamber 114, for example, via wash lines 130, a wash pump 132 and via a 3-way valve 134. Cleaning fluid 118 from a rinse tank 144, for example rinse fluid in the form of a rinse aid solution, can be supplied to the optional rinse nozzle system 124, for example, via rinse lines 138, a rinse valve 140 and a rinse pump 142. Fresh water, for example, can be fed to the rinse tank 144 via a fresh-water feed line 146. Furthermore, the cleaning device 110 can have a discharge line 148 which is connected to the wash tank 136 via the 3-way valve 134, for example, can optionally comprise a discharge pump 150 and can optionally be connected to an outflow 152.

Furthermore, the cleaning device 110 can have at least one heating element 154 for heating the cleaning fluid 118 in the wash tank 136. Furthermore, the cleaning device 110 can have a further heating element 156 in the rinse tank 144 for heating the cleaning fluid 118 which is received there and is in the form of rinse fluid. By way of example, the rinse tank 144 can be configured as a boiler and/or can have a flow heater or be connected to a flow heater.

A cleaning program, for example, can be executed in the cleaning device 110 which can be configured, for example, as a batch dishwasher. In said cleaning program, a first program step can be carried out for example, the items 116 to be cleaned being washed with liquid from the wash tank 136 in said first program step. This washing can be performed, for example, in a circulation mode via the wash pump 132 which can also be called a circulation pump. The wash liquid can then be completely or partially discharged from the wash tank 136 via the discharge pump 150 and the 3-way valve 134. In parallel with the wash step, rinse fluid can be prepared, for example heated, in the rinse tank 144 in advance. In a further program step which follows the wash step, the items 116 to be cleaned can then be subjected to rinsing or final-rinsing with cleaning fluid from the rinse tank 144, it being possible for this to be performed in a single operation or, optionally, likewise in a circulation mode. One or more further program steps can follow, for example one or more drying steps, before the cleaning program can be terminated.

The cleaning device 110 according to the exemplary embodiment which is illustrated in FIG. 1 comprises a plurality of electrical loads 158. Examples which can be mentioned in this case include, in particular, the heating elements 154, 156. Further exemplary embodiments in the example shown in FIG. 1 are the pumps 132, 142 and 150.

In order to supply electrical energy to said electrical loads, the cleaning device 110 is connected to an electrical connection 160. Furthermore, the cleaning device 110 has, according to this disclosure, one or more energy stores 162. By way of example, an electrical energy store 164 and/or a non-electrical energy store 166 are optionally illustrated in FIG. 1, it being possible for said energy stores to each have one or more energy converters 168. As described above, electrical power which is received via the electrical connection 160 can be temporarily stored in the energy store 162 in the form of electrical and/or non-electrical energy, before said energy is supplied to all of, individual ones of or several of the electrical loads 158. Reference can be made to the above description for possible refinements of the energy stores 162.

The cleaning device 110 can further comprise at least one controller 170 which can be configured in a central or decentral manner. This controller 170 can comprise, for example, at least one data-processing device. The controller 170 can be designed, for example, to control one or more cleaning programs and can accordingly drive, for example, the electrical loads 158 for this purpose. The controller 170 can comprise, for example, at least one user interface and/or at least one interface to another apparatus, it being possible for information and/or commands to be exchanged in a unidirectional or bidirectional manner via said interface.

The controller 170 can furthermore control the distribution of flows of energy within the cleaning device 110. By way of example, the controller 170 can be connected to at least one measuring device which is not illustrated in FIG. 1 and which can determine a current power requirement and/or a current power consumption. Accordingly, the controller 170 can, for example variably, charge the energy stores 162 individually, in groups or altogether with electrical energy which is received via the electrical connection 160 and/or can discharge the energy stores 162, wherein energy which is stored in the energy stores 162 is allocated to one, several or all of the electrical loads 158.

To this end, the cleaning device 110 can have one or more switching elements in this or else in other exemplary embodiments, said switching elements being denoted by the reference numerals 169 and 171 in FIG. 1. By way of example, at least one optional switching element 169 can be provided, this switching element setting, for example in a manner controlled by the controller 170, what proportion of the electrical power which is received from the electrical connection 160, without said electrical power being temporarily stored in the energy store 162, is supplied to the electrical loads 158, and what proportion of the electrical power which is received from the electrical connection 160 is temporarily stored in the energy store 162. These proportions can be set in a digital or analog manner and/or setting can be performed, as described above, continuously or in two or more stages. As an alternative or in addition, at least one switching element 171 can be provided, which switching element can, for example, set, once again for example in a manner controlled by the controller 170, the proportion with which the electrical loads 158 are currently being supplied with electrical energy from the energy store 162 and the proportion with which the electrical loads 158 are being supplied with electrical energy directly from the electrical connection 160 without said electrical energy being temporarily stored in the energy store 162. These proportions can also be set in a digital or analog manner and/or setting can be performed, as described above, continuously or in two or more stages. The at least one switching element 171 can also be configured with entirely or partially identical components to the at least one switching element 169. Furthermore, the switching elements 169, 171 and the energy stores 164, 166 can be of separate design or else can be completely or partially combined. Furthermore, the switching elements 169, 171 for the various loads 158 can be of separate design, or at least one of the switching elements 169, 171 can be provided for several loads 158 or even for all of the loads 158 together. The switching elements can comprise, for example, one or more relays, electronic relays, contactors, semiconductor contactors, power transistors and/or other types of switching elements.

By way of example, the controller can be designed to charge the energy stores 162 individually, several at a time or altogether in an operating phase of a downtime of the cleaning device 110. Furthermore, the controller 170 can be designed to supply energy which is stored in the energy store 162, optionally after being converted by the energy converter 168, to the electrical loads 158 in at least one operating phase in which cleaning fluid 118 is applied to the items 116 to be cleaned, as an alternative or in addition to electrical energy which is received directly via the electrical connection 160. Reference can be made to the above description for further possible refinements.

Figure 2:
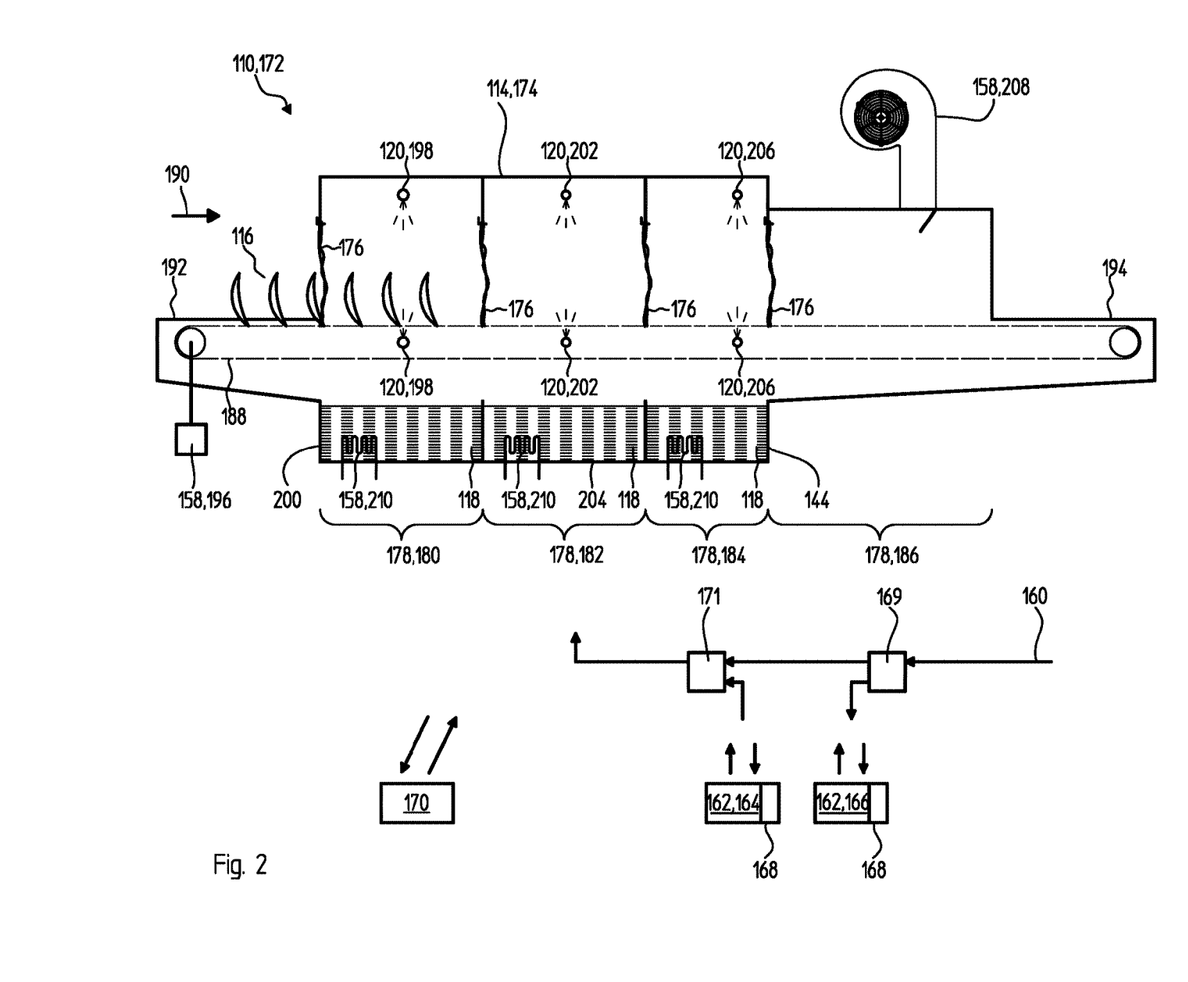
FIG. 2 shows a second exemplary embodiment of a cleaning device according to this disclosure in the form of a conveyor-type dishwasher.

FIG. 2 shows a sectional illustration through a further exemplary embodiment of a cleaning device 110 according to this disclosure from the side. In this exemplary embodiment, the cleaning device 110 is a conveyor-type dishwasher 172. Reference can be made, for example, to DE 10 2004 046 758 A1, DE 10 2007 053 381 B3 or DE 10 2009 035 668 A1, which are cited above, for possible refinements of conveyor-type dishwashers of this kind which can be modified and/or supplemented according to this disclosure. However, other refinements are also possible in principle.

In the illustrated exemplary embodiment, the cleaning device 110 once again has a cleaning chamber 114 in the form of a tunnel 174. The tunnel 174 is subdivided into several zones 178 by separating curtains 176, wherein a pre-clearing zone 180, a wash zone 182, a final-rinse zone 184 and a drying zone 186 are provided in the illustrated exemplary embodiment by way of example. A different configuration of the zones 178 is also possible.

In the illustrated exemplary embodiment, items 116 to be cleaned, for example once again in the form of dishes, are conveyed through the tunnel 174 in a transportation direction 190 by means of at least one transportation device 188. To this end, the cleaning device 110 can be configured, for example, as a belt-conveyor dishwasher or as a rack-conveyor dishwasher. By way of example, at least one inlet 192, at which the items 116 to be cleaned are transferred to the transportation device 188, and at least one outlet 194, at which the items 116 which have been cleaned can be removed, can be provided. The transportation device 188 can accordingly comprise, for example, a conveyor belt. Other refinements are also possible. The transportation device 188 can comprise, for example, at least one drive 196.

Cleaning fluid 118 is once again applied to the items 116, which are to be cleaned, by means of fluid devices 120 in the zones 180, 182 and 184. By way of example, a pre-clearing zone nozzle system 198 can be provided in the pre-clearing zone 180 for this purpose, it being possible for cleaning fluid to be fed to said pre-clearing zone nozzle system from a pre-clearing tank 200, for example, via a pump which is not illustrated in FIG. 2 and a line system which is not illustrated. By way of example, a wash zone nozzle system 202 can be provided in the wash zone 182, it being possible for cleaning fluid 118 to be fed to said wash zone nozzle system from a wash tank 204, for example, via a pump which is likewise not illustrated and a line system which is likewise not illustrated. By way of example, a rinse nozzle system 206 can be provided in the final-rinse zone 184 which can be configured in one part or else in the several parts, it being possible for heated fresh water and/or rinse fluid to be fed to said rinse nozzle system from a rinse tank 144.

After passing through the zones 180, 182 and 184, the items 116 which have been cleaned can then enter the drying zone 186 in which hot air can be applied to the items which have been cleaned, for example, by means of a fan 208 in order to accelerate drying of the items 116 which have been cleaned.

The cleaning device 110 in the illustrated exemplary embodiment once again has several electrical loads 158. By way of example, heating elements 210 can be provided in the tanks 200, 204 and 144 individually or in groups. Furthermore, the drive 196 of the transportation device 188 and the fan 208 can be considered to be electrical loads 158 in the illustrated exemplary embodiment, wherein the fan 208 can optionally comprise a heating device as a further electrical load 158. Furthermore, the pumps, which are not illustrated in FIG. 2, for supplying fluid to the fluid devices 120 can function as electrical loads 158.

In order to realize the teachings of this disclosure provided above, the cleaning device 110 can also once again comprise one or more energy stores 162 in the illustrated exemplary embodiment according to FIG. 2, for example once again in the form of electrical energy stores 164 and/or non-electrical energy stores 166. For example, electrical power can be received via an electrical connection 160 and this electrical power can be temporarily stored in the at least one energy store 162 or, optionally, supplied selectively directly to the electrical loads 158. A controller 170 which can set, for example, different operating states of the cleaning device 110 and which can ensure, for example, distribution of the electrical energy and implementation of a method according to this disclosure can once again be provided. To this end, one or more switching elements 169, 171 can once again be provided, for example, wherein reference can once again be made to the above description. By way of example, one or more of the energy stores 162 can be charged during relatively long downtimes of the cleaning device 110, for example overnight. When the machine is started up and the cleaning device 110 is moved to an operating state in which cleaning fluid 118 is applied to the items 110 to be cleaned, the energy which is temporarily stored in said energy store or stores can be supplied to one, to several or to all of the electrical loads 158. As stated above, it is possible to accelerate, for example, the process of making the cleaning device 110 ready for operation and/or to reduce the maximum power received in total in relation to conventional cleaning devices 110 in this way.

Figure 3:
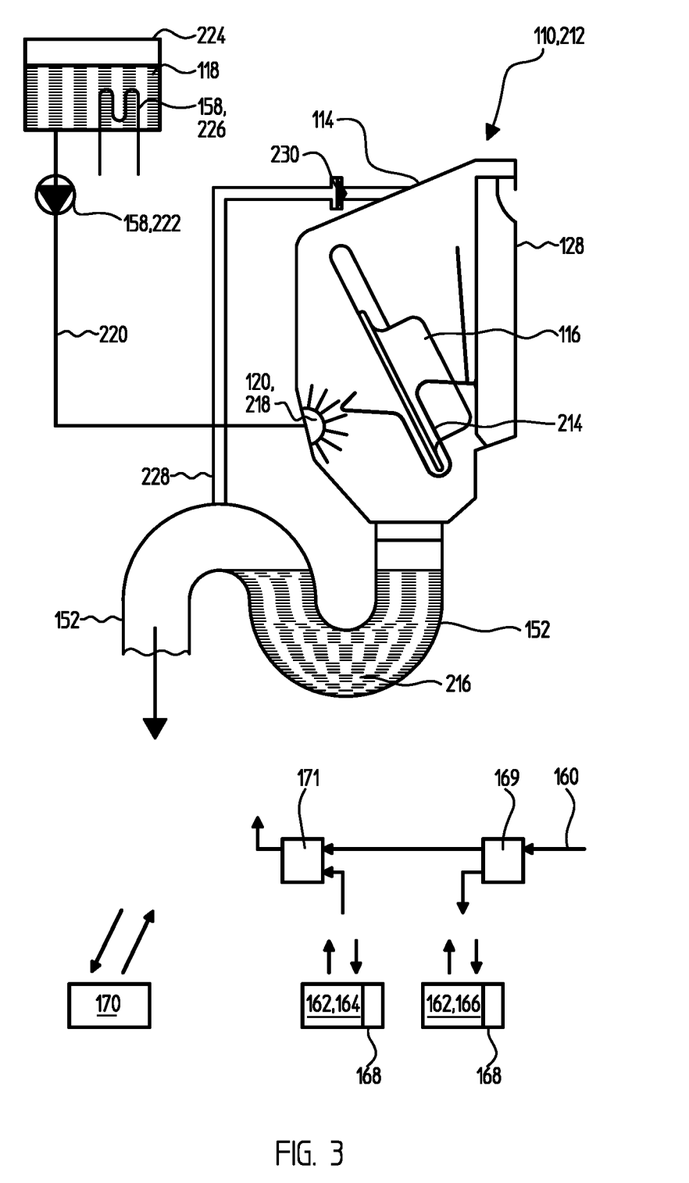
FIG. 3 shows a further exemplary embodiment of a cleaning device according to this disclosure in the form of a cleaning and disinfection apparatus.

FIG. 3 shows a sectional illustration through a third exemplary embodiment of a cleaning device 110 from the side. In this exemplary embodiment, the cleaning device 110 is configured as a cleaning and disinfection apparatus 212. The cleaning device 110 once again comprises a cleaning chamber 114 with a door 128, for example a front flap. Items 116 to be cleaned, for example in the form of one or more excretion vessels for receiving relatively large quantities of human or animal excreta, can be received in the cleaning chamber 114. These items 116 to be cleaned can be held, for example, in a corresponding holder 214. This holder 214 is preferably configured in such a way that, when the door 128 is closed, the items 116 to be cleaned are automatically emptied into an outflow 152 which can comprise, in particular, a siphon bend or another type of odor trap.

Cleaning fluid 118 can be applied to the items 116 to be cleaned in the cleaning chamber 114. To this end, a fluid device 120 can, for example, once again be provided in the form of a nozzle system 218. This nozzle system 218 can be fed with liquid from one or more tanks 224, for example, via a line system 220 and optionally a pump 222. In this case, different types of cleaning fluids 118 can also be used in succession. For example, cold, aqueous cleaning liquid can initially be applied to the items to be cleaned, for example after they are emptied into the outflow 152, and then heated, aqueous cleaning liquid, possibly with the addition of one or more detergents and/or one or more disinfectants, can be applied to said items in a further step. Superheated vapor can then optionally be applied to said items, it being possible for the cleaning device 110 to comprise, for example, a vapor generator, which is not illustrated in FIG. 3, for this purpose. Different cleaning fluids 118 can be applied by means of one and the same fluid system 120 or else by means of different fluid systems. One or more heating elements 226 can once again be provided in order to generate heated cleaning fluid 118 and/or in order to generate superheated vapor.

A drying phase can follow application of cleaning fluid 118 to the items 116 which have been cleaned. By way of example, fresh air or else hot air can be introduced into the cleaning chamber 114 during this drying phase, for example forcibly by means of a fan, which is not illustrated in FIG. 3. As fresh or heated air is forcibly introduced in this way, the moist air and/or vapor which are/is present in the cleaning chamber 114 can be forced into the outflow 252 via a bypass 228, optionally having a non-return valve 230, so as to bypass the odor trap or the siphon bend 216. In this way, it is possible to ensure that no moist air and no hot vapor can enter the surrounding area when the door 128 is opened.

The cleaning device 110 according to the exemplary embodiment in FIG. 3 can once again comprise a plurality of electrical loads 158. By way of example, the pump 222 and/or the heating element 226 can be configured as electrical loads 158 in FIG. 3. In order to supply electrical energy to these electrical loads 158, electrical energy is once again received by the cleaning device 110 via an electrical connection 160. One or more energy stores 162 are once again provided according to this disclosure, optionally once again with one or more energy converters 168 in which energy which has been received via the electrical connection 160 can be temporarily stored before being supplied to an electrical load 158. Accordingly, energy from the energy store 162 can be supplied to the electrical loads 158 and/or, as an alternative or in addition, electrical energy which has been received via the electrical connection 160 can be directly supplied to said electrical loads without said electrical energy being temporarily stored. A controller 170 can once again be provided in order to control the distribution of electrical energy, for example in accordance with a program sequence or a current operating state of the cleaning device. One or more switching elements 169, 171 can once again be provided, it being possible for reference to be made to the above description in respect of the possible configuration of said switching elements.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

LIST OF REFERENCE SYMBOLS

| | |
|---|---|
| 110 | Cleaning device |
| 112 | Single-chamber dishwasher |
| 114 | Cleaning chamber |
| 116 | Items to be cleaned/items which have been cleaned |
| 118 | Cleaning fluid |
| 120 | Fluid device |
| 122 | Wash nozzle system |
| 124 | Rinse nozzle system |
| 126 | Rack |
| 128 | Door |
| 130 | Wash lines |
| 132 | Wash pump |
| 134 | 3-way valve |
| 136 | Wash tank |
| 138 | Rinse lines |
| 140 | Rinse valve |
| 142 | Rinse pump |
| 144 | Rinse tank |
| 146 | Fresh water feed line |
| 148 | Discharge line |
| 150 | Discharge pump |
| 152 | Outflow |
| 154 | Heating element |
| 156 | Heating element |
| 158 | Electrical load |
| 160 | Electrical connection |
| 162 | Energy store |
| 164 | Electrical energy store |
| 166 | Non-electrical energy store |
| 168 | Energy converter |
| 169 | Switching element |
| 170 | Controller |
| 171 | Switching element |
| 172 | Conveyor-type dishwasher |
| 174 | Tunnel |
| 176 | Separating curtain |
| 178 | Zone |
| 180 | Pre-clearing zone |
| 182 | Wash zone |
| 184 | Final-rinse zone |
| 186 | Drying zone |
| 188 | Transportation device |
| 190 | Transportation direction |
| 192 | Inlet |
| 194 | Outlet |
| 196 | Drive |
| 198 | Pre-clearing zone nozzle system |
| 200 | Pre-clearing tank |
| 202 | Wash zone nozzle system |
| 204 | Wash tank |
| 206 | Rinse nozzle system |
| 208 | Fan |
| 210 | Heating element |
| 212 | Cleaning and disinfection apparatus |
| 214 | Holder |
| 216 | Siphon bend |
| 218 | Nozzle system |
| 220 | Line system |
| 222 | Pump |
| 224 | Tank |
| 226 | Heating element |
| 228 | Bypass |
| 230 | Non-return valve |

What is claimed is:

1. A cleaning device for cleaning items to be cleaned, comprising:
a fluid device for applying a cleaning fluid to the items to be cleaned;
a cleaning chamber in which the cleaning fluid is applied to the items to be cleaned;
an electrical load;

an electrical connection for supplying electrical energy to the cleaning device; and
an energy store;
wherein the cleaning device is operable to:
(a) receive electrical energy via the electrical connection and to temporarily store said electrical energy in the energy store;
(b) selectively supply electrical energy from the energy store to the electrical load and to selectively directly supply electrical energy received via the electrical connection to the electrical load; and
(c) simultaneously (i) supply electrical energy from the energy store to the electrical load and (ii) directly supply electrical energy which is received via the electrical connection to the electrical load; and
a controller configured to monitor electrical power received via the electrical connection and selectively supply electrical energy from the energy store to the electrical load to thereby prevent, under all operating conditions, the electrical power received via the electrical connection from exceeding a fixed specified maximum power.

2. The cleaning device as claimed in claim 1, wherein the cleaning device is operable to change the ratio between the electrical energy supplied from the energy store to the electrical load and the electrical energy which is received via the electrical connection and supplied to the electrical load.

3. The cleaning device as claimed in claim 2, wherein the cleaning device is operable to select the ratio based upon a current operating state.

4. The cleaning device as claimed in claim 1, wherein the cleaning device has an operating state wherein the cleaning device receives the electrical power via the electrical connection at the specified maximum power and temporarily stores in the energy store the difference between the specified maximum power and the total power currently required by the electrical load.

5. The cleaning device as claimed in claim 1, wherein the energy store has a storage capacity of at least 10 Wh.

6. The cleaning device as claimed in claim 1, wherein the cleaning device is selected from the group consisting of a dishwasher and a cleaning and disinfection apparatus.

7. The cleaning device as claimed in claim 1, wherein the cleaning device is operable in at least two different operating states, wherein the load has a different electrical power consumption in the operating states, wherein electrical energy is received via the electrical connection and the energy store is charged with electrical energy in at least a first operating state, and wherein electrical energy is drawn from the energy store and supplied to the electrical load in at least a second operating state.

8. The cleaning device as claimed in claim 7, wherein the first operating state comprises a downtime of the cleaning device during which no cleaning fluid is applied to the items to be cleaned.

9. The cleaning device as claimed in claim 1, wherein the energy store has at least one electrical energy store.

10. The cleaning device as claimed in claim 9, wherein the electrical energy store is selected from the group consisting of a rechargeable battery and a capacitor.

11. The cleaning device as claimed in claim 10, wherein the capacitor is a supercap.

12. The cleaning device as claimed in claim 9, wherein the electrical energy store is selected from the group consisting of a lead-acid rechargeable battery, a NiCd rechargeable battery, a NiMH rechargeable battery and a lithium-ion rechargeable battery.

13. The cleaning device as claimed in claim 1, wherein the energy store further comprises at least one non-electrical energy store.

14. The cleaning device as claimed in the claim 13, wherein the energy store comprises at least one energy converter operable to convert between electrical energy and at least one non-electrical form of energy, wherein the non-electrical form of energy is storable in the non-electrical energy store.

15. The cleaning device as claimed in claim 14, wherein the energy store comprises at least one or both of an electrolysis cell and a fuel cell as the energy converter.

16. The cleaning device as claimed in claim 13, wherein the non-electrical energy store comprises at least one heat store.

17. The cleaning device as claimed in claim 16, wherein the heat store is selected from the group consisting of a direct heat store and a latent heat store.

18. The cleaning device as claimed in claim 17, wherein the heat store is a water tank.

19. The cleaning device as claimed in claim 18, wherein the water tank has at least one of a thermal insulation or a heat pump.

20. The cleaning device as claimed in claim 16, wherein the heat store is a salt store.

21. The cleaning device as claimed in claim 13, wherein the non-electrical energy store comprises at least one mechanical energy store.

22. The cleaning device as claimed in claim 13, wherein the non-electrical energy store comprises at least one chemical energy store.

23. The cleaning device as claimed in claim 22, wherein the chemical energy store comprises at least one gas store.

24. The cleaning device as claimed in claim 23, wherein the gas store comprises at least one of a hydrogen store or oxygen store.

25. The cleaning device as claimed in claim 1, wherein the cleaning device is selected from the group consisting of a batch dishwasher and a conveyor-type dishwasher.

26. The cleaning device as claimed in claim 1 wherein the cleaning device is adapted such that, under some operating conditions, the at least one electrical load exceeds the fixed specified maximum power.

27. A method of using a cleaning device for cleaning items to be cleaned, comprising:
(a) supplying electrical energy via an electrical connection to an energy store of the cleaning device;
(b) storing said electrical energy temporarily in the energy store;
(c) supplying electrical energy from the energy store to at least one electrical load of the cleaning device;
(d) directly supplying electrical energy received via the electrical connection to the at least one electrical load;
(e) applying at least one cleaning fluid to the items to be cleaned by means of a fluid device; and
(f) limiting electrical power which is received via the electrical connection, under all operating conditions, to a fixed specified maximum power.

28. The method of claim 27, further comprising simultaneously conducting steps (c) and (d).

29. The method of claim 27, further comprising changing the ratio between the electrical energy supplied from the energy store to the electrical load and the electrical energy which is received via the electrical connection and supplied to the electrical load.

30. The method of claim 29, further comprising selecting the ratio based upon a current operating state.

31. The method of claim 27, further comprising temporarily storing in the energy store the difference between the specified maximum power and the total power currently required by the electrical load.

32. The method of claim 27 wherein, under some operating conditions, the at least one electrical load exceeds the fixed specified maximum power.

* * * * *